US009011850B2

(12) United States Patent
Ueno et al.

(10) Patent No.: US 9,011,850 B2
(45) Date of Patent: *Apr. 21, 2015

(54) METHOD OF STABILIZING ANTIBODY AND STABILIZED SOLUTION-TYPE ANTIBODY PREPARATION

(71) Applicant: Kyowa Hakko Kirin Co., Ltd, Tokyo (JP)

(72) Inventors: Yuji Ueno, Sunto-gun (JP); Takashi Kayashita, Sunto-gun (JP); Atsushi Ishihara, Sunto-gun (JP); Masashi Nakakura, Sunto-gun (JP); Kyoko Yamauchi, Sunto-gun (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/918,507

(22) Filed: Jun. 14, 2013

(65) Prior Publication Data

US 2013/0280248 A1 Oct. 24, 2013

Related U.S. Application Data

(63) Continuation of application No. 10/574,016, filed as application No. PCT/JP2004/014903 on Oct. 1, 2004, now Pat. No. 8,496,930.

(30) Foreign Application Priority Data

Oct. 1, 2003 (JP) .................................. 2003-343645

(51) Int. Cl.
*A61K 39/395* (2006.01)
*A61K 47/18* (2006.01)
*A61K 9/00* (2006.01)
*A61K 47/12* (2006.01)

(52) U.S. Cl.
CPC ............. *A61K 47/183* (2013.01); *A61K 9/0019* (2013.01); *A61K 39/39591* (2013.01); *A61K 47/12* (2013.01)

(58) Field of Classification Search
None
See application file for complete search history.

(56) References Cited

U.S. PATENT DOCUMENTS

| 4,721,777 | A | 1/1988 | Uemura et al. | |
|---|---|---|---|---|
| 6,169,070 | B1 | 1/2001 | Chen et al. | |
| 6,437,098 | B1 | 8/2002 | Shitara et al. | |
| 6,488,930 | B1 | 12/2002 | Wu et al. | |
| 8,496,930 | B2 * | 7/2013 | Ueno et al. | 424/130.1 |
| 2003/0190316 | A1 | 10/2003 | Kakuta et al. | |

FOREIGN PATENT DOCUMENTS

| EP | 0597101 A1 | 5/1994 |
|---|---|---|
| EP | 1174148 A1 | 1/2002 |
| EP | 1254666 A1 | 11/2002 |
| EP | 1314437 A1 | 5/2003 |
| FR | 2708467 A1 | 2/1995 |
| JP | 62-194459 A | 8/1987 |
| JP | 62-244441 A1 | 10/1987 |
| JP | 06-189781 | 7/1994 |
| JP | 7-502497 | 3/1995 |
| JP | 9-500894 | 1/1997 |
| WO | 93/08837 A1 | 5/1993 |
| WO | 93/22335 A1 | 11/1993 |
| WO | 95/03826 A1 | 2/1995 |
| WO | 96/07429 A1 | 3/1996 |
| WO | 99/37329 A1 | 7/1999 |
| WO | 00/66160 A1 | 11/2000 |
| WO | 00/67791 A1 | 11/2000 |
| WO | 03/063767 A2 | 8/2003 |

OTHER PUBLICATIONS

Supplementary Search Report issued in European Patent Application No. 04773700.2 on Aug. 21, 2008.
Bao-Lu Chen et al., "Strategies to suppress aggregation of recombinant Keratinocyte growth factor during liquid formulation development", Journal of Pharmaceutical Sciences, 1994, 83(12): 1657-1661.
Glycine Material Safety Data Sheet (MSDS), Mallinckrodt chemicals, 2005, retrieved from http://www.jtbaker.com/msds/englishhtml/g5828.htm on Jul. 30, 2008, 6 pages.
Junji Kanazawa et al., "Therapeutic potential of chimeric anti-(ganglioside GD3) antibody KM871: Antitumor activity in xenograft model of melanoma and effector function analysis" Cancer Immunol. Immunother., 2000, 49(4-5): 253-258.
Yu-Chang John Wang et al., "Parenteral Formulations of Proteins and Peptides: Stability and Stabilizers", Journal of Parenteral Science & Technology, 1988, 42: S4-S26.
Wei Wang et al., "Protein aggregation and its inhibition in biopharmaceutics", International Journal of Pharmaceutics, 2005, 289: 1-30.

* cited by examiner

*Primary Examiner* — Yunsoo Kim
(74) *Attorney, Agent, or Firm* — Sughrue Mion, PLLC

(57) ABSTRACT

The present invention provides a method of suppressing the formation of a soluble association of an antibody in a solution; a method of suppressing the formation of a chemically degraded product of an antibody in a solution; and a method of stabilizing an antibody in a solution. The present invention also provides a solution-type antibody preparation in which the formation of a soluble association is suppressed; a solution-type antibody preparation in which the formation of a chemically degraded product is suppressed; a solution-type antibody preparation in which the formation of a soluble association, the formation of a chemically degraded product and the formation of an insoluble aggregate are suppressed; an agent for suppressing the formation of a soluble association of an antibody; an agent for suppressing the formation of a chemically degraded product of an antibody; and a stabilizing agent for an antibody.

10 Claims, No Drawings

METHOD OF STABILIZING ANTIBODY AND STABILIZED SOLUTION-TYPE ANTIBODY PREPARATION

This is a continuation of U.S. patent application Ser. No. 10/574,016 filed Mar. 29, 2006, which is a 371 National Stage Entry of PCT/JP04/14903 filed Oct. 1, 2004, which claims priority to Japanese Patent Application No. 2003-343645 filed Oct. 1, 2003, the contents of all of which are incorporated herein by reference in their entirety.

TECHNICAL FIELD

The present invention relates to a method for stabilizing an antibody in a solution and a stabilized solution-type antibody preparation.

BACKGROUND ART

In recent years, treatment of a disease using an antibody has rapidly been adopted through the advance of biotechnology. Also in Japan, various antibody preparations such as Synagis, Remicade, Rituxan and Herceptin are provided in the medical field.

When an antibody is stored in a solution for a long time, the formation of a chemically degraded product, the formation of an insoluble aggregate, the formation of a soluble association or the like occurs. Therefore, in order to provide a stable and safe antibody drug, there has been a demand for a method of suppressing the formation of such substances.

When an antibody is stored in a state of a solution for a long time, a chemical degradation reaction such as cleavage of a disulfide bond or a peptide bond of an antibody occurs. As a result, there is concern for a decrease in its activity, an unexpected side effect or the like due to the deterioration in the quality thereof.

Protein is insolubilzed through aggregation of molecules whose higher-order structure is disrupted with disrupted high-order structure due to shaking, heat stress, or the like. When such an insoluble aggregate is intravenously administered, a serious side effect such as anaphylactic shock is liable to occur (Japanese Published Unexamined Patent Application No. 502938/98).

As the method of suppressing the formation of an insoluble aggregate, a method of adding citric acid at 100 mmol/L or more or heparin at 0.5% to antibody solution in order to suppress the formation of an insoluble aggregate caused by heat stress in an aqueous solution of a recombinant human keratinocyte growth factor is known (Journal of Pharmaceutical Science, Vol. 83, No. 12, 1657-1661 (1994)). Further, as the method of suppressing the formation of an insoluble aggregate caused by heat stress in an aqueous solution of an antibody, a method using a glycine buffer or a histidine buffer (WO 02/13860), a method of adding polyvinylpyrorridone at 2% or more (Pharmaceutical Research Vol. 11, No. 5, 624-632, 1994), a method of adding a phosphate buffer, sodium chloride and maltose (Japanese Published Unexamined Patent Application No. 504499/91), and the like are known.

Although some proteins may not lead to insolubilization, they are known to form a soluble association comprising a small number of protein molecule such as a dimer or a trimer. For example, when the protein is an antibody, it is considered that a soluble dimer is easily formed (Biochemistry, Vol. 38, 13960-13967 (1999)). In addition, when a dimer of an antibody is administered into the human body, there is a risk of causing a side effect such as fever, nausea or hypotension (Japanese Published Unexamined Patent Application No. 502938/98).

As the method for suppressing the formation of a soluble association, a method of adding a nicotinic acid derivative or an α-amino acid having a lipophilic side chain as a stabilizing agent into a liquid immunoglobulin preparation is known (Japanese Published Unexamined Patent Application No. 502938/98).

As described above, there has been a demand for a method of providing a stable antibody preparation which achieves the stabilization of the antibody in a solution by overcoming plural factors of instability such as the formation of a chemically degraded product, the formation of an insoluble aggregate and the formation of a soluble association. However, such a method has not been known so far.

DISCLOSURE OF THE INVENTION

An object of the present invention is to provide a method of suppressing the formation of a soluble association of an antibody in a solution; a method of suppressing the formation of a chemically degraded product of an antibody in a solution; and a method of stabilizing an antibody in a solution. Further, another object of the present invention is to provide a solution-type antibody preparation in which the formation of a soluble association is suppressed; a solution-type antibody preparation in which the formation of a chemically degraded product is suppressed; a solution-type antibody preparation in which the formation of a soluble association, the formation of a chemically degraded product and the formation of an insoluble aggregate are suppressed; an agent for suppressing the formation of a soluble association of an antibody; an agent for suppressing the formation of a chemically degraded product of an antibody; and a stabilizing agent for an antibody.

The present invention relates to the following (1) to (25).
(1) A method for stabilizing an antibody in a solution, which comprises adding glycine and citric acid to the antibody in a solution.
(2) The method according to the above (1), wherein the method of stabilizing an antibody is suppression of the formation of a soluble association and a chemically degraded product of the antibody in a solution.
(3) A method for suppressing the formation of a soluble association of an antibody in a solution, which comprises adding glycine to the antibody in a solution.
(4) A method for suppressing the formation a chemically degraded product of an antibody in a solution, which comprises adding citric acid to the antibody in a solution.
(5) The method according to any one of the above (1) to (4), wherein concentration of the antibody is at 0.01 to 150 mg/mL.
(6) The method according to any one of the above (1) to (3), wherein concentration of the glycine is at 10 to 30 mg/mL.
(7) The method according to any one of the above (1), (2) and (4), wherein concentration of the citric acid is at 0.1 to 50 mmol/L.
(8) The method according to any one of the above (1) to (7), further comprising a nonionic surfactant.
(9) The method according to any one of the above (1) to (8), wherein the pH of the solution is within the range of 4 to 7.
(10) The method according to any one of the above (1) to (9), wherein the antibody is a humanized antibody or a human antibody.
(11) The method according to any one of the above (1) to (10), wherein the antibody is any one of antibodies to ganglioside GD3 and antibodies to CC chemokine receptor 4 (hereinafter referred to as CCR4).

(12) A solution-type antibody preparation in which the formation of a soluble association of the antibody is suppressed, comprising glycine and the antibody.

(13) A solution-type antibody preparation in which the formation of a chemically degraded product of the antibody is suppressed, comprising citric acid and the antibody.

(14) A solution-type antibody preparation in which the formation of a soluble association, a chemically degraded product and an insoluble aggregate of the antibody are suppressed, comprising glycine, citric acid and the antibody.

(15) The preparation according to any one of the above (12) to (14), wherein concentration of the antibody is at 0.01 to 150 mg/mL.

(16) The preparation according to any one of the above (12), (14) and (15), wherein concentration of the glycine is at 10 to 30 mg/mL.

(17) The preparation according to any one of the above (13) to (15), wherein concentration of the citric acid is at 0.1 to 50 mmol/L.

(18) The preparation according to any one of the above (12) to (17), further comprising a nonionic surfactant.

(19) The preparation according to any one of the above (12) to (18), wherein the pH of the solution is within the range of 4 to 7.

(20) The preparation according to any one of the above (12) to (19), wherein the antibody is a humanized antibody or a human antibody.

(21) The preparation according to any one of the above (12) to (20), wherein the antibody is any one of antibodies to ganglioside GD3 and antibodies to CCR4.

(22) An agent for suppressing the formation of a soluble association of an antibody in a solution, which comprises glycine as an active ingredient.

(23) An agent for suppressing the formation of a chemically degraded product of an antibody in a solution, which comprises citric acid as an effective component.

(24) A stabilizing agent for an antibody, which comprises glycine and citric acid as active ingredient.

(25) The stabilizing agent for an antibody according to the above (24), wherein the stabilization of the antibody is suppression of the formation of a soluble association, a chemically degraded product and an insoluble aggregate of the antibody in a solution.

The antibody to be used in the present invention also includes an antibody fragment. Such an antibody and an antibody fragment include a polyclonal antibody and a monoclonal antibody, however, a monoclonal antibody is preferred.

Further, the above-mentioned antibody or antibody fragment include a non-human animal antibody, a recombinant antibody, an antibody fragment thereof and the like.

Examples of the recombinant antibody include a humanized antibody, a human antibody and the like, and examples of the humanized antibody include a human chimeric antibody, a human CDR-grafted antibody and the like.

The human chimeric antibody refers to an antibody comprising VH and VL of a non-human animal antibody, and CH and CL of a human antibody. As the CH of a human chimeric antibody, any CH can be used as long as it belongs to human immunoglobulin (hereinafter referred to as hIg), however, those belonging to the hIgG class are preferred and any one of the subclasses belonging to the hIgG class such as hIgG1, hIgG2, hIgG3 and hIgG4 can be used. Further, as the CL of a human chimeric antibody, any CL can be used as long as, it belongs to the hIg, and those belonging to a κ class or a λ class can be used.

Further, examples of the non-human animal include a mouse, a rat, a hamster, a rabbit and the like.

The human CDR-grafted antibody refers to an antibody in which the CDRs of VH and VL of a non-human animal antibody are grafted into an appropriate position in VH and VL of a human antibody.

The human CDR-grafted antibody of the present invention can be produced by designing and constructing cDNAs encoding V regions in which CDRs of VH and VL of a non-human animal antibody are ligated to the frameworks (hereinafter referred to as FR(s)) of VH and VL of an optional human antibody, inserting them into an expression vector for an animal cell having cDNAs encoding CH and CL of a human antibody, respectively, to thereby construct a human CDR-grafted antibody expression vector, and then introducing the expression vector into an animal cell to express the human CDR-grafted antibody.

As the CH of a human CDR-grafted antibody, any CH can be used as long as it belongs to the hIg, however, those belonging to the hIgG class are preferred and any one of the subclasses belonging to the hIgG class such as hIgG1, hIgG2, hIgG3 and hIgG4 can be used. Further, as the CL of a human CDR-grafted antibody, any CL can be used as long as it belongs to the hIg, and those belonging to a κ class or a λ class can be used.

The human antibody is originally an antibody naturally existing in the human body, however it also includes antibodies obtained from a human antibody phage library and a human antibody-producing transgenic animal, which are prepared based on the recent progress in genetic engineering, cell engineering and developmental engineering techniques. The antibody existing in the human body can be obtained, for example, by isolating a human peripheral blood lymphocyte, immortalizing it by infecting with EB virus or the like, followed by cloning, thereby obtaining a lymphocyte producing the antibody, and then culturing the lymphocyte and purifying the antibody from the culture supernatant. The human antibody phage library is a library in which an antibody fragment such as Fab or scFv is expressed on the surface of a phage by inserting an antibody gene prepared from a human B cell into the phage gene. A phage which expresses an antibody fragment having a desired antigen binding activity on its surface can be recovered from the library by using the binding activity to a substrate having an antigen immobilized thereon as the index. The, antibody fragment can be further converted into a human antibody molecule comprising two full length H chains and two full length L chains by genetic engineering techniques. The human antibody-producing transgenic animal is an animal in which a human antibody gene has been introduced into its cell. Specifically, a human antibody-producing transgenic mouse can be produced, for example, by introducing a human antibody gene into a mouse ES cell, transplanting the ES cell into an early stage embryo of a mouse, then developing. As a method for preparing a human antibody from such a human antibody-producing transgenic animal, the human antibody can be produced and accumulated in a culture supernatant by culturing a human antibody-producing hybridoma obtained by a method for preparing hybridoma, generally carried out in a non-human animal.

Examples of the antibody fragment to be used in the present invention include Fab, Fab', F(ab')$_2$, scFv, diabody, dsFv, a peptide containing CDR and the like.

The Fab is an antibody fragment having a molecular weight of about 50,000 and having an antigen-binding activity, in which about a half of the N-terminal side of H chain and the full length L chain, among fragments obtained by treating an IgG type antibody molecule with a protease, papain (cleaving at the amino acid residue at position 224 of the H chain), are bound together through a disulfide bond.

The Fab to be used in the present invention can be obtained by treating an antibody with a protease, papain. Alternatively, the Fab can be produced by inserting DNA encoding Fab of the antibody into an expression vector for prokaryote or an expression vector for eukaryote, and introducing the vector into a prokaryote or a eukaryote to express the Fab.

The F(ab')$_2$ is an antibody fragment having a molecular weight of about 100,000 and having an antigen-binding activity, which is slightly larger than the Fab bound via a disulfide bond of the hinge region, among fragments obtained by treating an IgG-type antibody molecule with a protease, pepsin (cleaving at the amino acid residue at position 234 of the H chain).

The F(ab')$_2$ to be used in the present invention can be obtained by treating an antibody with a protease, pepsin. Alternatively, the F(ab')$_2$ can be prepared by binding Fab' described below via a thioether bond or a disulfide bond.

The Fab' is an antibody fragment having a molecular weight of about 50,000 and having an antigen-binding activity, in which the disulfide bond of the hinge region of the above F(ab')$_2$ is cleaved.

The Fab' to be used in the present invention can be obtained by treating F(ab')$_2$ with a reducing agent, dithiothreitol. Alternatively, the Fab' can be produced by inserting DNA encoding a Fab' fragment of the antibody into an expression vector for prokaryote or an expression vector for eukaryote, and introducing the vector into a prokaryote or a eukaryote to express the Fab'.

The scFv is a VH-P-VL or a VL-P-VH polypeptide in which one chain VH and one chain VL are linked using an appropriate peptide linker (hereinafter referred to as P) and an antigen fragment having an antigen-binding activity.

The scFv to be used in the present invention can be produced by obtaining cDNAs encoding VH and VL of the antibody, constructing DNA encoding the scFv, inserting the DNA into an expression vector for prokaryote or an expression vector for eukaryote, and then introducing the expression vector into a prokaryote or a eukaryote to express the scFv.

The diabody is an antibody fragment in which scFv is dimerized, and has a divalent antigen-binding activity. The diabody can have a divalent antigen binding activity to the same antigen or to different antigens. The diabody to be used in the present invention can be produced by obtaining cDNAs encoding VH and VL of the antibody, constructing DNA encoding scFv such that the length of the amino acid sequence of a linker is not more than 8 residues, inserting the DNA into an expression vector for prokaryote or an expression vector for eukaryote, and then introducing the expression vector into a prokaryote or a eukaryote to express the diabody.

The dsFv is an antibody fragment in which polypeptides prepared by substituting one amino acid residue in each of VH and VL with a cysteine residue are linked via a disulfide bond between the cysteine residues. The amino acid residue to be substituted with a cysteine residue can be selected based on a three-dimensional structure estimation of the antibody in accordance with the method shown by Reiter et al. (Protein Engineering, 7, 697-704 (1994)). The dsFv to be used in the present invention can be produced by obtaining cDNAs encoding VH and VL of the antibody, constructing DNA encoding dsFv, inserting the DNA into an expression vector for prokaryote or an expression vector for eukaryote, and then introducing the expression vector into a prokaryote or a eukaryote to express the dsFv.

The peptide containing CDR comprises at least one region of CDR of VH or VL. A peptide containing plural CDRs can be linked directly or via an appropriate peptide linker. The peptide containing CDR to be used in the present invention can be produced by constructing DNAs encoding CDRs of VH and VL of the antibody, inserting the DNAs into an expression vector for prokaryote or an expression vector for eukaryote, and then by introducing the expression vector into a prokaryote or a eukaryote to express the peptide. Further, the peptide containing CDR can also be produced by a chemical synthetic method such as an Fmoc method (fluorenylmethoxycarbonyl method) or a tBoc method (t-butyloxycarbonyl method).

The antibody to which the present invention can be applied may be any antibody, however, specific examples include a monoclonal antibody to ganglioside GD3, a monoclonal antibody to CCR4 and the like. Examples of the monoclonal antibody to ganglioside GD3 include a mouse monoclonal antibody KM-641 (Japanese Patent No. 3006943), a human chimeric antibody KM-871 (Japanese Publised unexamined Patent Application No 304989/93), a human CDR-grafted antibody KM-8871 (WO 01/23432) and the like. Examples of the monoclonal antibody to CCR4 include a human chimeric antibody KM2760 (WO 01/64754), an anti-CCR4 human CDR-grafted antibody KM8760 (WO 03/18635) and the like.

In the present invention, the chemically degraded product refers to a substance resulting from the cleavage of a disulfide bond or a peptide bond of an antibody. Specific examples include those in which a part or the whole of the H chain or the L chain of the antibody has been lost. Further, the Fab fragment described above, those in which the H chain and the L chain of the Fab fragment have been further cleaved and the like are also included.

In the present invention, the insoluble aggregate refers to an insolubilized substance resulting from the aggregation of molecules whose water solubility has been significantly lowered because the hydrophobicity of the surface of the molecules has increased due to the change of the higher-order structure of the molecules or the like. Accordingly, by the formation of the insoluble aggregate, the turbidity of a solution-type antibody preparation is increased.

In the present invention, the soluble association refers to a substance in which antibody molecules are associated with each other, but the higher-order structure of the antibody molecules has not changed or the change of the higher-order structure is relatively minor, whereby the water solubility of the aggregate is maintained to a degree that it is not deposited in an aqueous solution. Accordingly, an increase in the turbidity of a preparation is not increased by the formation of such a soluble association. In general, the number of antibody molecules to be associated with each other is relatively small, and it is usually a dimer, a trimer or a tetramer.

A method of producing the solution-type antibody preparation of the present invention is not particularly limited as long as it is a method which is carried out in the production of a general solution-type antibody preparation. Specifically, it can be produced by preparing a solution containing an antibody and a solution containing an additive in advance and mixing the solutions. It can also be produced by directly adding an antibody or an additive material to a solvent and dissolving it therein.

In the method of stabilizing an antibody in a solution, the method of suppressing the formation of a soluble association in a solution and the method of suppressing the formation of a chemically degraded product in a solution of the present invention, the antibody concentration may be any value as long as it is in the range of 0.01 to 150 mg/mL, however, it is preferably at 0.1 to 50 mg/mL, more preferably 1 to 20 mg/mL.

In the method of stabilizing an antibody in a solution and the method of suppressing the formation of a soluble association in a solution of the present invention, the amount of glycine to be added may be any concentration as long as the glycine concentration is in the range of 10 to 30 mg/mL, it is preferably at 20 to 25 mg/mL, more preferably 22 to 23 mg/mL. Examples of the form of glycine to be added include glycine, pharmaceutically acceptable salts of glycine such as glycine hydrochloride and the like.

In the method of stabilizing an antibody in a solution, and the method of suppressing the formation of a chemically degraded product in a solution of the present invention, the amount of citric acid to be added may be any concentration as long as the citric acid concentration is in the range of 0.1 to 50 mmol/L, but it is preferably at 0.5 to 20 mmol/L, more preferably 1 to 10 mmol/L. Examples of the form of citric acid to be added include citric acid, pharmaceutically acceptable salts of citric acid such as sodium citrate and the like.

The method for stabilizing an antibody in an antibody solution of the present invention has an effect on the suppression of the formation of a soluble association, a chemically degraded product and an insoluble aggregate of the antibody in a solution.

The antibody concentration in the preparation of the present invention may be any concentration as long as it is in the range of 0.01 to 150 mg/mL, but it is preferably at 0.1 to 50 mg/mL, more preferably 1 to 20 mg/mL.

The content of glycine in the present invention may be any content as long as the glycine concentration is in the range of 10 to 30 mg/mL, but it is preferably in the range of 20 to 25 mg/mL, more preferably 22 to 23 mg/mL. Examples of the form of glycine to be added include glycine, pharmaceutically acceptable salts of glycine such as glycine hydrochloride and the like.

The content of citric acid in the present invention may be any content as long as the citric acid concentration is in the range of 0.1 to 50 mmol/L, but it is preferably in the range of 0.1 to 50 mmol/L, more preferably 1 to 10 mmol/L. Examples of the form of citric acid to be added include citric acid, pharmaceutically acceptable salts of citric acid such as sodium citrate and the like.

The preparation of the present invention may comprise a nonionic surfactant in addition to the above-mentioned antibody, glycine and citric acid, and preferred examples include sorbitan fatty acid esters, polyoxyethylene sorbitan fatty acid esters, polyoxyethylene polyoxypropylene glycols, polyoxyethylene hydrogenated castor oils, polyethylene glycol fatty acid esters, glycerine fatty acid esters, sucrose fatty acid esters and the like. Particularly preferred examples include polyoxyethylene sorbitan monolaurate (polysorbate 20), polyoxyethylene sorbitan monooleate (polysorbate 80) and the like. The nonionic surfactant concentration is not particularly limited as long as it is in a pharmaceutically acceptable concentration, but it is preferably at 0.01 to 10 mg/mL, more preferably 0.05 to 1 mg/mL, most preferably 0.1 to 0.3 mg/mL.

It is preferred that the pH of the preparation of the present invention is controlled to be an appropriate value. As the appropriate pH, it is preferably at pH 4 to 7, more preferably pH 5 to 6. As for the pH, any of various pharmaceutically acceptable pH regulators such as hydrochloric acid, sulfuric acid, phosphoric acid, citric acid, acetic acid, lactic acid, tartaric acid, sodium hydroxide and potassium hydroxide can be used.

Further, in the preparation of the present invention, a pharmaceutically acceptable additives as illustrated below may be added.

Examples of a tonicity adjusting agent include inorganic salts such as sodium chloride, potassium chloride, sodium hydrogen phosphate and sodium dihydrogen phosphate; sugars and sugar alcohols such as glucose, fructose, lactose, maltose, trehalose, mannitol, sorbitol and xylitol; glycerin, dextran, propylene glycol, polyethylene glycol, nicotinamide and the like.

Examples of a analgesic agent include inositol, chlorobutanol, propylene glycol, benzyl alcohol, lidocaine, magnesium sulfate and the like.

Examples of a preservative include parabens such as methyl p-hydroxybenzoate and ethyl p-hydroxybenzoate; benzoic acid, ethanol, tetrasodium edetate, citric acid, salicylic acid, sorbitol, sorbic acid, glycerin, chlorobutanol, phenol, propylene glycol, benzyl alcohol and the like.

Examples of a viscosity controlling agent include sodium alginate, xanthan gum, glycerin, gelatin, dextran, dextrin, cellulose alkyl ethers such as hydroxypropyl cellulose and hydroxypropylmethyl cellulose; polyethylene glycol, polyvinyl alcohol.

Examples of an antioxidant include erythorbic acid, dibutylhydroxytoluene, butylhydroxyanisol, sodium thioglycolate, α-tocopherol, tocopherol acetate, L-ascorbic acid, sodium bisulfite, sodium sulfite, sodium pyrosulfite, cysteine hydrochloride, sodium edetate and the like.

A preferred administration method for the preparation of the present invention is injection, however, a percutaneous, transmucosal, transnasal, pulmonary, oral or other administration forms can also be employed. A particularly preferred administration method by means of injection is a method of intravenous, subcutaneous or intramuscular injection. In addition, by using an appropriate administration device, it can be directly administered to a lesion region such as a tumor region or an inflammatory region.

Further, the preparation of the present invention can be used after it is diluted with a diluent at the time of use. Examples of the diluent include infusions such as a physiological saline solution and a sugar solution. The diluted preparation can be administered into the body while the rate is controlled by intravenous infusion or by using a syringe pump or the like.

The solution-type antibody preparation of the present invention can be used as an injection by sterilizing the preparation by a standard technique such as aseptic filtration followed by packaging it into an injectable container such as an ampoule, a vial or a syringe in an aseptic environment. Further, when the solution-type antibody preparation is packaged in a container, gas replacement in the space of the container can also be performed by using an inert gas such as nitrogen or argon.

Hereinafter the present invention will be specifically described with reference to Examples, however, the present invention is not limited to these Examples.

BEST MODE FOR CARRYING OUT THE INVENTION

Example 1

Preparation of Sample Preparation

Each of the solution compositions of formulations 1 to 5 shown in Table 1 was prepared, subjected to aseptic filtration, injected into a glass vial, and then sealed with a rubber stopper and an aluminum cap, whereby a sample preparation was prepared. All these operations were carried out under an aseptic environment. As for an antibody, a human chimeric antibody to ganglioside GD3 KM-871, which was produced by the method described in Japanese Published Unexamined Patent Application No. 304989/93 was used.

TABLE 1

| | Antibody concentration (mg/mL) | Additive | pH |
|---|---|---|---|
| Formulation 1 | 2 | Phosphoric acid: 10 mmol/L | 6 |
| Formulation 2 | 2 | Citric acid: 10 mmol/L | 6 |
| Formulation 3 | 2 | Citric acid: 10 mmol/L Mannitol: 50 mg/mL | 6 |
| Formulation 4 | 2 | Citric acid: 10 mmol/L Glycine: 23 mg/mL | 6 |
| Formulation 5 | 2 | Citric acid: 10 mmol/L Glycine: 23 mg/mL Polysorbate 80: 0.1 mg/mL | 6 |

Example 2

Stability Test

Each sample preparation prepared in Example 1 was stored at 40° C. for 1 month, and then, a stability test was carried out for the following test items.
(1) Visual Observation of Content
The content of each sample preparation was visually observed under white fluorescent lights while it is gently stirred, and the presence or absence of turbidity was determined.
(2) Turbidity Measurement
The content of each sample preparation was collected in a quartz micro cell, and the absorbance at a wavelength of 400 nm (O.D.400) was measured with an ultraviolet spectrophotometer (Hitachi U-3300).
(3) Gel Filtration HPLC
An analysis by HPLC under the following conditions was carried out for the content of each sample preparation.
(HPLC conditions)
Column: TSKgel G3000 SWXL (Tosoh Co.)
Mobile phase: 0.5 mol/L phosphate buffer containing 0.3 mol/L sodium chloride
Measurement wavelength: 280 nm
Flow rate: 1 mL/min
Injected amount: 40 μL
Apparatus: LC-10A system (Shimadzu Corporation)
The sum of the peak areas of the components eluted on the higher molecular weight side of the peak of the unchanged molecule on the HPLC chart was regarded as the peak area of soluble associations, and the content of the soluble associations was calculated by the following equation (1).

(Content of soluble associations(%))=(Peak area of soluble associations)/(Total peak area)×100     (1)

Further, the sum of the peak areas of the components eluted on the lower molecular weight side of the peak of the unchanged molecule on the HPLC chart was regarded as the peak area of chemically degraded products, and the content of the chemically degraded products was calculated by the following equation (2).

(Content of chemically degraded products(%))=(Peak area of chemically degraded products)/(Total peak area)×100     (2)

The results of the (1) visual observation of the content and the (2) turbidity (O.D.400) measurement are shown in Table 2. In Table 2, the value of the turbidity (O.D.400) indicates the amount of increase during the storage period (40° C., 1 month), which was obtained by subtracting the initial value from the measurement value.

TABLE 2

| | Storing at 40° C. for 1 month | |
|---|---|---|
| | Presence or absence of turbidity (visual observation) | Amount of increase of O.D.400 |
| Formulation 1 | Absence | 0.002 |
| Formulation 2 | Absence | 0.000 |
| Formulation 3 | Absence | 0.002 |
| Formulation 4 | Absence | 0.002 |
| Formulation 5 | Absence | 0.002 |

From the results of the visual observation of the content in all formulations (formulations 1 to 5), turbidity was not observed. Further, in all formulations, an increase in the turbidity (O.D.400) was rarely observed.

The results of gel filtration HPLC are shown in Table 3. The value shown in Table 3 indicates the amount of increase during the storage period (40° C., 1 month), which was obtained by subtracting the initial value from the measurement value.

TABLE 3

| | Amount of increase after storing at 40° C. for 1 month | |
|---|---|---|
| | Soluble associations (%) | Chemically degraded products (%) |
| Formulation 1 | 0.20 | 1.48 |
| Formulation 2 | 0.20 | 0.59 |
| Formulation 3 | 0.22 | 0.47 |
| Formulation 4 | 0.02 | 0.51 |
| Formulation 5 | 0.04 | 0.42 |

On the comparison of the formulation 1 (phosphoric acid) with the formulations 2 and 3 (citric acid), the amount of increase of the chemically degraded products in the formulations 2 and 3 was smaller than that in the formulation 1. From the above results, it was found that by adding citric acid to a solution, an increase in the chemically degraded products can be reduced.

Further, on the comparison of the formulation 2 with the formulation 4, the amount of increase of soluble associations in the formulation 4 was smaller than that in the formulation 2, and it was found that by the addition of glycine to a solution, an increase in the soluble associations can be reduced.

Also in the formulation 5 obtained by further adding polysorbate 80 to the formulation 4, the stability of the solution was maintained.

Example 3

Confirmation of Effect on Suppressing Insoluble Aggregates 1 (Preparation of Sample)

Each of the solution compositions of formulations 7 to 11 shown in Table 4 was prepared, filtered through a filter with a pore size of 0.2 μm, and then injected into a glass test tube. The test tube was sealed with a silicon stopper, whereby a sample preparation was prepared. As for an antibody, a human chimeric antibody to ganglioside GD3 KM-871 disclosed in Japanese Published Unexamined Patent Application No. 304989/93 was used.

TABLE 4

|  | Antibody concentration (mg/mL) | Additive | pH |
|---|---|---|---|
| Formulation 7 | 2 | Phosphoric acid: 50 mmol/L | 6 |
| Formulation 8 | 2 | Citric acid: 0.1 mmol/L Glycine: 10 mg/mL | 6 |
| Formulation 9 | 2 | Citric acid: 0.1 mmol/L Glycine: 30 mg/mL | 6 |
| Formulation 10 | 2 | Citric acid: 50 mmol/L Glycine: 10 mg/mL | 6 |
| Formulation 11 | 2 | Citric acid: 50 mmol/L Glycine: 30 mg/mL | 6 |

Example 4

Confirmation of Effect on Suppressing Insoluble Aggregates 1 (Stability Test)

Each sample preparation prepared in Example 3 was stored at 70° C. for 270 seconds, and then, a stability test was carried out for the following test items.
(1) Visual Observation of Content
The content of each sample preparation was visually observed under white fluorescent lights while it was gently stirred, and the presence or absence of turbidity was determined.
(2) Turbidity Measurement
The content of each sample preparation was collected in a quartz micro cell, and the absorbance at a wavelength of 400 nm (O.D.400) was measured with an ultraviolet spectrophotometer (Hitachi U-3300).
The results of the (1) visual observation of the content and the (2) turbidity (O.D.400) measurement are shown in Table 5.

TABLE 5

| | After storing at 70° C. for 270 seconds | |
|---|---|---|
|  | Presence or absence of turbidity (visual observation) | O.D.400 |
| Formulation 7 | Apparent white turbidity | 2.471 |
| Formulation 8 | Absence | 0.009 |
| Formulation 9 | Absence | 0.011 |
| Formulation 10 | Absence | 0.020 |
| Formulation 11 | Absence | 0.033 |

In the formulation 7, apparent white turbidity was observed as the result of the visual observation, and the turbidity (O.D.400) also showed a high value. On the other hand, in the formulations 8, 9, 10 and 11, turbidity was not observed as the result of the visual observation of the content, and it was confirmed that the values of turbidity (O.D.400) are significantly lower than that of the formulation 7.

Example 5

Confirmation of Effect on Suppressing Insoluble Aggregates 2 (Preparation of Sample)

Each of the solution compositions of formulations 12 to 16 shown in Table 6 was prepared, filtered through a filter with a pore size of 0.2 μm, and then injected into a glass test tube. The test tube was sealed with a silicon stopper, whereby a sample preparation was prepared. As for an antibody, a human CDR-grafted antibody to CCR4 disclosed in WO 03/18635, KM8760 was used.

TABLE 6

|  | Antibody concentration (mg/mL) | Additive | pH |
|---|---|---|---|
| Formulation 12 | 2 | Phosphoric acid: 50 mmol/L | 6 |
| Formulation 13 | 2 | Citric acid: 0.1 mmol/L Glycine: 10 mg/mL | 6 |
| Formulation 14 | 2 | Citric acid: 0.1 mmol/L Glycine: 30 mg/mL | 6 |
| Formulation 15 | 2 | Citric acid: 50 mmol/L Glycine: 10 mg/mL | 6 |
| Formulation 16 | 2 | Citric acid: 50 mmol/L Glycine: 30 mg/mL | 6 |

Example 6

Confirmation of Effect on Suppressing Insoluble Aggregates 2 (Stability Test)

Each sample preparation prepared in Example 5 was stored at 70° C. for 210 seconds, and then, a stability test was carried out for the following test items.
(1) Visual Observation of Content
The content of each sample preparation was visually observed under white fluorescent lights while it is gently stirred, and the presence or absence of turbidity was determined.
(2) Turbidity Measurement
The content of each sample preparation was collected in a quartz micro cell, and the absorbance at a wavelength of 400 ma (O.D.400) was measured with an ultraviolet spectrophotometer (Hitachi U-3300).
The results of the (1) visual observation of the content and the (2) turbidity (O.D.400) measurement are shown in Table 7.

TABLE 7

| | After storing at 70° C. for 210 seconds | |
|---|---|---|
|  | Presence or absence of turbidity (visual observation) | O.D.400 |
| Formulation 12 | Apparent white turbidity | 0.698 |
| Formulation 13 | Absence | 0.079 |
| Formulation 14 | Absence | 0.006 |
| Formulation 15 | Absence | 0.056 |
| Formulation 16 | Absence | 0.024 |

In the formulation 12, apparent white turbidity was observed as the result of the visual observation, and the turbidity (O.D.400) also showed a high value. On the other hand, in the formulations 13, 14, 15 and 16, turbidity was not observed as the result of the visual observation of the content, and it was confirmed that the values of turbidity (O.D.400) are significantly lower than that of the formulation 12.

Example 7

Confirmation of Effect on Suppressing Soluble Associations and Chemically Degraded Products (Preparation of Sample)

Each of the solution compositions of formulations 17 to 21 shown in Table 8 was prepared, subjected to aseptic filtration, injected into a glass vial, and then sealed with a rubber stopper and an aluminum cap, whereby a sample preparation was prepared. All these operations were carried out under an aseptic environment. As for an antibody, a human CDR-grafted antibody to CCR4 disclosed in WO 03/18635, KM8760 was used.

TABLE 8

| | Antibody concentration (mg/mL) | Additive | pH |
|---|---|---|---|
| Formulation 17 | 2 | Phosphoric acid: 50 mmol/L | 6 |
| Formulation 18 | 2 | Citric acid: 0.1 mmol/L Glycine: 10 mg/mL | 6 |
| Formulation 19 | 2 | Citric acid: 0.1 mmol/L Glycine: 30 mg/mL | 6 |
| Formulation 20 | 2 | Citric acid: 50 mmol/L Glycine: 10 mg/mL | 6 |
| Formulation 21 | 2 | Citric acid: 50 mmol/L Glycine: 30 mg/mL | 6 |

Example 7

Confirmation of Effect on Suppressing Soluble Associations and Chemically Degraded Products (Stability Test)

Each sample preparation prepared in Example 8 was stored at 40° C. for 1 month, and then, the stability was evaluated by analyzing the content by gel filtration HPLC under the following conditions.

(HPLC conditions)
Column: TSKgel G3000 SWXL (Tosoh Co.)
Mobile phase: 0.05 mol/L phosphate buffer containing 0.3 mol/L sodium chloride
Measurement wavelength: 280 nm
Flow rate: 1 mL/min
Injected amount: 40 μL
Apparatus: LC-10A system (Shimadzu Corporation)

The sum of the peak areas of the components eluted on the higher molecular weight side of the peak of the unchanged molecule on the HPLC chart was regarded as the peak area of soluble associations, and the content of the soluble associations was calculated by the following equation.

(Content of soluble associations(%))=(Peak area of soluble associations)/(Total peak area)×100　　(1)

Further, the sum of the peak areas of the components eluted on the lower molecular weight side of the peak of the unchanged molecule on the HPLC chart was regarded as the peak area of chemically degraded products, and the content of the chemically degraded products was calculated by the following equation.

(Content of chemically degraded products(%))=(Peak area of chemically degraded products)/(Total peak area)×100　　(2)

The results of gel filtration HPLC are shown in Table 9. The results show the increased amount during the storage period (40° C., 1 month), which was obtained by subtracting the initial value from the measurement value.

TABLE 9

Amount of increase after storing at 40° C. for 1 month

| | Soluble associations (%) | Chemically degraded products (%) |
|---|---|---|
| Formulation 17 | 0.11 | 0.96 |
| Formulation 18 | −0.02 | 0.44 |
| Formulation 19 | 0.02 | 0.47 |
| Formulation 20 | −0.05 | 0.35 |
| Formulation 21 | 0.05 | 0.38 |

As the result of comparing the formulation 17 with the formulations 18, 19, 20 and 21, it was found that the formulations 18, 19, 20 and 21 have an excellent stability in view of both the soluble associations and the chemically degraded products.

Example 9

Confirmation of Stability of Preparation (Preparation of Sample)

A solution composition of a formulation 22 shown in Table 10 was prepared, subjected to aseptic filtration, injected into a glass vial, and then sealed with a rubber stopper and an aluminum cap, whereby a sample preparation was prepared. All these operations were carried out under an aseptic environment. As for an antibody, a human CDR-grafted antibody to CCR4 disclosed in WO 03/18635, KM8760 was used.

TABLE 10

| | Antibody concentration (mg/mL) | Additive | pH |
|---|---|---|---|
| Formulation 22 | 4 | Phosphoric acid: 2 mmol/L Glycine: 22.5 mg/mL Polysorbate 80: 0.2 mg/mL | 5.5 |

Example 10

Confirmation of Stability of Preparation (Storing at 40° C.)

The sample preparation prepared in Example 9 was stored at 40° C. for 1 month, and then, the stability was evaluated by analyzing the content by gel filtration HPLC under the following conditions.

(HPLC conditions)
Column: TSKgel G3000 SWxL (Tosoh Co.)
Mobile phase: 0.05 mol/L phosphate buffer containing 0.3 mol/L sodium chloride
Measurement wavelength: 280 nm
Flow rate: 1 mL/min
Injected amount: 40 μL
Apparatus: LC-10A system (Shimadzu Corporation)

The sum of the peak areas of the components eluted on the higher molecular weight side of the peak of the unchanged molecule on the HPLC chart was regarded as the peak area of soluble associations, and the content of the soluble associations was calculated by the following equation (1).

(Content of soluble associations(%))=(Peak area of soluble associations)/(Total peak area)×100　　(1)

Further, the sum of the peak areas of the components eluted on the lower molecular weight side of the peak of the unchanged molecule on the HPLC chart was regarded as the peak area of chemically degraded products, and the content of the chemically degraded products was calculated by the following equation (2).

(Content of chemically degraded products(%))=(Peak area of chemically degraded products)/(Total peak area)×100  (2)

The results of gel filtration HPLC are shown in Table 11. The results show the amount of increase during the storage period (40° C., 1 month), which was obtained by subtracting the initial value from the measurement value.

TABLE 11

Amount of increase after storing at 40° C. for 1 month

|  | Soluble associations (%) | Chemically degraded products (%) |
|---|---|---|
| Formulation 22 | −0.02 | 0.46 |

It was confirmed that the formulation 22 comprising citric acid and glycine has an excellent stability in view of both the soluble associations and the chemically degraded products.

Example 11

Confirmation of Stability of Preparation (Storing at 70° C.)

The content of the preparation prepared in Example 9 was filtered through a filter with a pore size of 0.2 μm, and then injected into a glass test tube. The opening of the test tube was sealed with a stopper, whereby a sample was prepared. The sample was stored at 70° C. for 210 seconds, and then, a stability test was carried out for the following test items.
(1) Visual Observation of Content
The content of each sample preparation was visually observed under white fluorescent lights while it is gently stirred, and the presence or absence of turbidity was determined.
(2) Turbidity Measurement
The content of each sample preparation was collected in a quartz micro cell, and the absorbance at a wavelength of 400 nm (O.D.400) was measured with an ultraviolet spectrophotometer (Hitachi U-3300).
The results of the (1) visual observation of the content and the (2) turbidity (O.D.400) measurement are shown in Table 12.

TABLE 12

After storing at 70° C. for 210 seconds

|  | Presence or absence of turbidity (visual observation) | O.D.400 |
|---|---|---|
| Formulation 22 | Absence | 0.014 |

It was confirmed that the formulation 22 which is a preparation comprising citric acid and glycine has an excellent stability in view of the insoluble aggregates as well.

INDUSTRIAL APPLICABILITY

According to the present invention, a method of stabilizing an antibody in a solution and a stabilized solution-type antibody preparation can be provided.

The invention claimed is:

1. A method for producing an antibody solution in which the formation of soluble dimers and trimers of antibody is inhibited, wherein said method comprises the step of:
    suppressing the formation of soluble dimers and trimers of an antibody by combining, in a solution, 10 to 30 mg/ml glycine, 0.1 to 50 mmol/L citric acid, and the antibody, to produce an antibody solution in which the formation of soluble dimers and trimers of the antibody is inhibited.
2. The method according to claim 1, wherein the concentration of the antibody in said antibody solution is 0.01 to 150 mg/mL.
3. The method according to claim 1, wherein said antibody solution further comprises a nonionic surfactant.
4. The method according to claim 1, wherein said antibody solution has a pH of between 4 and 7.
5. The method according to claim 1, wherein the antibody is a humanized antibody or a human antibody.
6. The method according to claim 5, wherein the antibody is an antibody to ganglioside GD3 or an antibody to CCR4.
7. The method according to claim 1, wherein the antibody is an IgG antibody.
8. The method according to claim 1, wherein the antibody is an IgG antibody, wherein the concentration of the antibody in said antibody solution is 0.01 to 150 mg/mL, and wherein the antibody solution has a pH of between 4 and 7.
9. The method according to claim 2, wherein the concentration of the antibody in said antibody solution is 0.1 to 50 mg/ml.
10. The method according to claim 9, wherein the concentration of the antibody in said antibody solution is 1 to 20 mg/ml.

* * * * *